(12) United States Patent
Chen

(10) Patent No.: US 7,041,316 B2
(45) Date of Patent: May 9, 2006

(54) STABLE ORAL PHARMACEUTICAL DOSAGE FORMS

(75) Inventor: Jivn-Ren Chen, Shreveport, LA (US)

(73) Assignee: Sage Pharmaceuticals, Inc., Shreveport, LA (US)

( * ) Notice: Subject to any disclaimer, the term of this patent is extended or adjusted under 35 U.S.C. 154(b) by 490 days.

(21) Appl. No.: 10/422,338

(22) Filed: Apr. 24, 2003

(65) Prior Publication Data

US 2003/0203018 A1    Oct. 30, 2003

Related U.S. Application Data

(60) Division of application No. 09/141,476, filed as application No. PCT/US98/09449 on May 8, 1998, now Pat. No. 6,726,927, which is a continuation-in-part of application No. 08/950,432, filed on Oct. 15, 1997, now abandoned.

(60) Provisional application No. 60/046,089, filed on May 9, 1997.

(51) Int. Cl.
| | |
|---|---|
| *A61L 9/48* | (2006.01) |
| *A61L 9/64* | (2006.01) |
| *A61L 9/20* | (2006.01) |
| *A61L 9/32* | (2006.01) |
| *A61L 9/14* | (2006.01) |

(52) U.S. Cl. ............... 424/463; 424/451; 424/456; 424/464; 424/474; 424/478; 424/480; 424/482; 424/489; 514/925; 514/962

(58) Field of Classification Search ............... 424/463, 424/451, 456, 464, 474, 478, 480, 482, 489; 514/925, 962

See application file for complete search history.

(56) References Cited

U.S. PATENT DOCUMENTS

| | | | |
|---|---|---|---|
| 4,670,287 A | * | 6/1987 | Tsuji |
| 4,786,505 A | * | 11/1988 | Lovgren et al. |
| 4,910,021 A | * | 3/1990 | Davis et al. |
| 5,178,867 A | * | 1/1993 | Guittard et al. |
| 6,013,281 A | * | 1/2000 | Lundberg et al. |

FOREIGN PATENT DOCUMENTS

| | | | |
|---|---|---|---|
| WO | 95/01783 | * | 1/1995 |

* cited by examiner

*Primary Examiner*—Thurman K. Page
*Assistant Examiner*—Humera N. Sheikh
(74) *Attorney, Agent, or Firm*—Jackson Walker L.L.P.

(57) ABSTRACT

The present invention relates to new stable enteric coated pharmaceutical dosage forms for oral use containing Omeprazole or Lansoprazole, to a formulation and a method for the manufacture of such a dosage forms, and to a method of gastric acid pump inhibition and providing gastrointestinal cytoprotective benefit by using them.

14 Claims, No Drawings

STABLE ORAL PHARMACEUTICAL DOSAGE FORMS

This is a divisional application of prior U.S. patent application Ser. No. 09/141,476 filed Aug. 27, 1998, now U.S. Pat. No. 6,726,927 which claims the priority of PCT/US98/09449, filed May 8, 1998, which is a continuation-in-part of U.S. patent application Ser. No. 08/950,432, filed Oct. 15, 1997, now abandoned, which claims the priority of U.S. Provisional Application No. 60/046,089, filed May 9, 1997, the content of which are incorporated by reference into this application.

BACKGROUND OF THE INVENTION

U.S. Pat. No. 4,255,431 describes a compound 2-[2-(3, 5-dimethyl-4-methoxy)-pyridyl methyl sulfinyl]-(5-methoxy)-benzimidazole (Omeprazole) or pharmaceutically acceptable salt or non-toxic acid addition salt as a therapeutic compound for mammals including man, suffering from gastric acid secretion disturbances.

Omeprazole, however is only stable in basic pH conditions and degrades rapidly in neutral or acid pH environment. For this reason the omeprazole oral dosage form must be protected, not only from the acidic inert ingredients used to make a dosage form but also from the acidic gastric fluid in order to intactly reach the absorption site in the small intestine.

A study [Drug Dev. Ind. Pharm. 21(8), 965 (1995)] showed the effect of pH on the stability of omeprazole solution. The pH-decomposition rate profile curve indicated that the maximum stability was at pH 11. Below pH 7.8 the decomposition was very fast.

A survey of the stability of Omeprazole products from 13 countries was reported [Drug Dev. Ind. Pharm. 22(12), 1173(1996)]. The results of this independent survey of the stability of omeprazole solid dosage forms (20 mg) show that product available in many countries worldwide exhibits a very wide range of stability characteristics. Only 18% of very wide range of stability characteristics. Only 18% of total products tested (34) were considered to demonstrate good physical and chemical stability over the course of the study.

U.S. Pat. No. 4,628,098 discloses that: Lansoprazole is a substituted benzimidazole 2-[[[3-methyl-4-(2,2,2-trifluroethoxy)-2-pyridyl]methyl]sulfinyl] benzimidazole, a compound and a pharmacologically acceptable salt thereof that inhibits gastric acid secretion.

Lansoprazole is relatively stable when exposed to light. The compound degrades in aqueous solution, the rate of degradation increasing with decreasing pH.

It is well known in the pharmaceutical industry that an enteric coating technology is the most efficient means to protect acid unstable medication from the attack of the gastric fluid and can rapidly release the active drug in the proximal part of the gastrointestinal canal.

An enteric coated dosage form of omeprazole was reported in 1985 by Pilbrant and Cederberg (Scand. J. Gastroenterology 1985; 20 (supp.108) p. 113–120). It was found later that the stability of this dosage form was not sufficient for a long term commercial purpose.

Because of the acidic property of the enteric coating polymer, the omeprazole or lansoprazole will degrade and diminish its therapeutic value by direct or indirect contact with it during or after the coating process, even in the presence of alkaline inert ingredients with the active drug in the core particles. enteric coating as the second layer to release the active drug in the colon.

WO number 85/03436 describes a technique to mix active drug with buffering components (i.e. sodium dihydrogen phosphate) to maintain a constant pH in a core for particular purposes. The core is coated with a layer which controls the diffusions.

All of these inventions when applied to omeprazole's or lansoprazole's case will not give either an adequate release of active drug or storage stability of such dosage form.

U.S. Pat. No. 4,786,505 teaches an art to make an oral pharmaceutical preparation comprising (1) a core consisting of omeprazole plus an alkaline reacting compound (2) an inert subcoating of core (3) an enteric coating of subcoated core and to use it in the treatment of gastrointestinal disease.

This technique requires a series of cumbersome and laborious pharmaceutical processes: 1) preparation of the core, which should be suitable for multilayer coating 2) Coating the core with one or more layers of an inert subcoating containing one or more alkaline substances 3) applying an outer enteric coating to the subcoated core 4) make the pharmaceutical preparation for therapeutical use.

U.S. Pat. No. 5,232,706 claims an oral pharmaceutical preparation of omeprazole or an alkali salt of omeprazole and a process for producing such preparation. The design principle of the preparation is basically similar to the U.S. Pat. No. 4,786,505. This preparation is comprised of: 1) a nucleus of active drug and first basic organic compound; 2) a first coating of nucleus containing at least a layer of a basic water soluble excipient and a second basic organic compound; and 3) a second coating formed by an enteric coating.

The major difference between U.S. Pat. No. 5,232,706 and U.S. Pat. No. 4,786,505 is the type of basic compound used; the former uses basic organic compound the later uses inorganic alkaline reaction compounds in core and in subcoating.

U.S. Pat. No. 5,385,739 relates to a stable formulation of Omeprazole microgranules containing a neutral core of sugar and starch coated with an active layer of drug and mannitol powder mixture with the aid of a solution of a binding agent in water plus ethanol. An additional protective layer of mannitol and sugar syrup is then applied prior to the final gastroprotection coating.

The art of coating a powder mixture containing an active ingredient onto the core of sugar and starch by using a binding solution is a rather difficult process to obtain uniform drug core granules.

In addition, two applications of aqueous solution involving the direct contact with Omeprazole, in the coating process, may effect the stability of this moisture-sensitive drug.

U.S. Pat. No. 5,399,700 teaches a method for stabilizing an acid unstable benzimidazole derivative, by forming an inclusion complex of Omeprazole with cyclodextrin.

This inclusion complex was synthesized in an aqueous alkaline solution at 40°–70° C. and then used to manufacture a tablet which is first coated by a water soluble substance and then with an enteric substance to form an enteric coated oral drug.

The safety of cyclodexrin for human oral dosage form needs to be clarified. Even if the acid stability and dissolution characterization of this inclusion complex has been well demonstrated in vitro, its behavior in vivo is not referenced in this patent.

U.S. Pat. No. 4,689,333 claims a pharmaceutical composition for preventing or treating digestive ulcers or gastritis which contains an effective amount of Lansoprazole or a pharmacologically acceptable salt thereof and pharmacologically acceptable carriers.

A study [Drug Dev. Ind. pharm. 18 (13), 1437 (1992)] reported that enteric granule formulations for Lansoprazole was established, however, it was difficult because some of the excipients needed for these formulations are incompatible with the drug. The alkaline stabilizers were then screened and the optimal pH stability of 9 was suggested in this paper.

A continued study from the above mentioned effort [Drug Dev. Ind. pharm. 20(9), 1661 (1994)] attempted to prepare more stable enteric granules without using these troublesome excipients by using a centrifugal fluid-bed granulator instead of an extruder-spheronizer. It was said that with this method more stable enteric granules could be obtained. The utilization of special sophisticated equipment to achieve the stable granules may suffer economical disadvantages.

U.S. Pat. No. 5,026,560 discloses spherical granules having a seed core coated with a binder and spraying powder containing lansoprazole as active drug, low substituted hydroxypropylcellulose and magnesium or calcium carbonate as alkaline agents. The powder coated core is further coated with spraying powder of low substituted hydroxypropylcellulose and then with enteric coating agent.

Technically, powder coating in pharmaceutical manufacturing brings forth issues such as content uniformity of the active on the seed core, laborious process attention and time consumption. It therefore tremendously increases the cost of the product.

U.S. Pat. No. 5,045,321 describes a pharmaceutical composition for coated tablets or granules, which is comprised of lansoprazole being in contact with at least one of the basic inorganic salts evenly. No protective and/or enteric coating is mentioned in the patent claim.

U.S. Pat. No. 5,093,132 is similar to the U.S. Pat. No. 5,045,321 but more specifically, describes an oral stabilized pharmaceutical composition for the inhibition of gastric acid secretion comprising of lansoprazole or its pharmaceutically acceptable salt in contact evenly with a basic inorganic salt stabilizing agent. It also mentions simply an enteric coating for the composition.

Enteric coated oral solid dosage forms have been in existence for a century. U.S. Pat. Nos. 3,656,997 and 3,959,540 disclosed a coated gastric juic resistant capsules and process for the production thereof. Most commercially available products under this category are coated pellets or granule filled capsules and tablet dosage forms. The concept of an enteric coated capsule dosage for commercial purposes are relatively new. So far, only one prescription product— VIVOTIF BERNA™ (Berna Products, Co., Coral Gables, Fla.) is in the U.S.A. market.

The advantage of enteric coated capsules are duplex. In addition to the merit natures of enteric coating polymers, the problem involved and the need for extensive efforts in development and the preparation of enteric pellets or tablets can be avoided.

Historically, enteric coated hard shell capsules were manufactured with formaldehyde treatments. This technology results in a stability problem with this product. Since the successful introduction of a number of enteric polymeric materials, the technology of this coating becomes more popular and is increasingly used in the pharmaceutical industry. However, the use of organic solvents causes risks of air pollution and inflammability. With the advent and availability of aqueous enteric polymer dispersions, manufacturing of enteric coated dosage forms have acquired a great deal of attention. The modern coating equipment now offers to pharmaceutical manufacturers better conditions for the application of aqueous coatings.

The process of enteric coating for pharmaceutical dosage forms are not significantly different with other coating processes. Generally, the sample is first placed in the coating pan or in the fluid-bed chamber for fluidization, while a coating solution is then spraying through a gun according to the two operations: 1) spraying or wetting and 2) drying, which is repeated consecutively during the process.

SUMMARY OF THE INVENTION

It is well known that the stability of omeprazole and lansoprazole may be affected adversely in the presence of water and organic solvent, especially by the former.

The previous art of U.S. Pat. No. 4,786,505 and number 5,232,706 all use conventional aqueous wet technologies to make core pellets or granulations. This invention, by preferably using dry mixing of drugs with alkaline substances as core granulations for either capsule filling or direct tablet compression in its processes, can substantially eliminate the stability risk of the active by excluding the moisture from the core granulation.

The alkaline substances in contact with the enteric coating in the aqueous environment can reduce the acid resistance properties of the latter. The invention of the above mentioned two U.S. patents includes the alkaline substances in the subcoating which is directly in contact with the enteric coating, thus it could be detrimental to the gastric fluid resistance of the enteric coating and result in the inferior therapeutic efficacy of omeprazole or lansoprazole.

For this reason the present invention uses a capsule shell as a separating barrier between the alkaline core of active drug and the enteric coatings. In the case of a tablet, only the pure, non-ionic polymer is used as a protective coating.

Furthermore, the present invention describes an improved oral pharmaceutical dosage form for omeprazole, its salt, lansoprazole or its salts. It is comprised of 1) a core powder or granules of active drug and alkaline inorganic or organic substances is formed by dry mixing; 2) said powder or granulation is filled into a hard gelatin capsule or is further mixed with other pharmaceutical excipients for direct tablet compression; 3) (for tablet only) a conventional pharmaceutical protective coating is disposed on the tablets; and 4) an outer layer of enteric coating is disposed on the dosage form (capsule or tablet).

This improved dosage form is more economically feasible in terms of time process and material savings. It is sufficiently stable for commercial distribution and storage. It also effectively protects the active drug from the attack of the acidic gastric fluid and efficiently delivers the active drug to the small intestine.

A process for the manufacturing of an oral dosage form of omeprazole or lansoprazole was also described. The details of granulation, encapsulation, tabletting and coating art can be found in "The Theory and Practice of Industrial Pharmacy, 1986, Lea & Febiger, Philadelphia, Pa., USA, the content of which is incorporated into this application as a reference.

DETAILED DESCRIPTION OF THE INVENTION

This is an invention of an improved pharmaceutical dosage form for oral administration to human being or animal host which is comprised of: (a) a core granulation formed by dry mixing an acid-unstable drug or its salt and an alkaline substance or pharmaceutical excipient without using an aqueous granulating solution; (b) said dry core granulation can then be quantitatively filled into a proper size empty hard gelatin capsule shell using this shell as a barrier and hence eliminating the process of applying a protective coating layer onto the granulation. In other words, this hard gelatin capsule shell constitutes simultaneously a barrier between said core granulation and the outer enteric coating of said capsule during the processing to complete the capsule dosage form; and (c) an enteric coating can then be applied onto said capsule to prevent the capsule from releasing the acid-unstable drug in a low pH environment (i.e. stomach) and then to deliver the drug in a higher pH environment (i.e. small intestine).

As used herein, core granulation is a mixture of a pharmaceutically acceptable granulated alkaline substance and, or excipient, and a drug active ingredient that can be processed into uniform spherelike or regularly shaped aggregates for the improvement of flowability and compressibility. The manufacturing processes may employ one, or a combination of, four established methods:

1) dry mixing;
2) direct compression;
3) milling; and
4) non-aqueous granulation.

These methods are described in "The Theory and Practice of Industrial Pharmacy, 1986, Lea & Febiger, Philadelphia, Pa., USA, edited by Lachman, L., Lieberman, H. A., and Kanig, J. L.

This invention also includes an improved pharmaceutical dosage form for oral administration to human being or animal host which consists of: (a) a core granulation formed by dry mixing an acid-unstable drug or its salt, and an alkaline substance or pharmaceutical excipient, without using an aqueous granulating solution, and which can be directly compressed into a tablet; (b) said tablet can then be filled into an empty, hard gelatin capsule shell using this shell as a barrier and hence eliminating the process of applying a protective layer onto the tablet. In other words, this hard gelatin capsule shell constitutes simultaneously a barrier between the said tablet and an outer enteric coating of said capsule during the processing to complete the capsule dosage form; and (c) an enteric coating can then be applied onto said capsule to prevent the capsule from releasing the acid-unstable drug in the low pH environment (i.e. stomach) and then to deliver the drug in a higher pH environment (i.e. small intestine).

Also included in this invention is an improved pharmaceutical dosage form for oral administration to human being or animal host which consists of: (a) a core granulation formed by dry mixing an acid-unstable drug or its salt, and an alkaline substance or pharmaceutical excipient, without using an aqueous granulating solution, which can then be directly compressed into a tablet; (b) said tablet can then be coated with a non-ionic protective coating in an orgainc solvent as a barrier: (1) to separate the acid-unstable active drug in the tablet from the outer enteric coating and, (2) to protect the outer enteric coating from the permeation of generated alkaline solution formed by any existed water in the core tablet; and (c) an enteric coating then can be applied onto said tablet to protect it from releasing the acid-unstable drug in a low pH environment (i.e. the stomach) and to deliver the active in a higher pH environment (i.e. the small intestine).

The protective coating can be applied by a standard film coating procedure in a suitable coating machine using a non-aqueous solution. The non-ionic protective polymer is selected from the group consisting of hydroxypropyl methylcellulose, hydroxyethyl cellulose, hydroxypropyl cellusose, and polyvinylpyrrolidone. The organic solvent is selected from the group consisting of isopropyl alcohol, methanol and ethanol. Other appropriate non-ionic protective polymer may be similarly used.

The plasticizer for protective coating includes, but is not limited to, triethyl citrate, propylene glycol and polyethylene glycol 6000.

In a preferred embodiment, the drug active ingredient comprises Omeprazole, salt of Omeprazole—selected from the group consisting of sodium, potassium, calcium and ammonium salts, Lansoprazole or salt of Lansoprazole.

In another embodiment, the alkaline substance of dosage form mentioned above comprises one or any combination of the following: (a) alkaline metallic salt of carbonic acid: calcium carbonate, granulated calcium carbonate; (b) dicalcium phosphate anhydrous, Dibasic sodium phosphate anhydrous, tricalcium phosphate, anhydrous; (c) sodium carboxymethylcellulose, calcium carboxymethylcellulose; (d) magnesium aluminum silicate; (e) sodium lauryl sulfate; (f) sodium bicarbonate; and (g) microcrystalline cellulose, hydroxypropylmethylcellulose, hydroxyethylcellulose.

Also in another embodiment, the pharmaceutical excipient mentioned in the above dosage forms may be selected from one or any combination of the group consisting of dextrose, sorbitol, mannitol, starch, dextrin, maltodextrin, lactose, magnesium stearate, calcium stearate, talc, microcrystalline cellulose, hydroxypropylmethylcellulose and hydroxyethylcellulose.

Also in another embodiment, the pharmaceutical excipient mentioned in the above dosage forms may be selected from one or any combination of the group consisting of dextrose, sorbitol, mannitol, starch, dextrin, maltodextrin, lactose, magnesium stearate, calcium stearate, talc, microcrystalline cellulose, hydroxypropylmethylcellulose and hydroxyethylcellulose. Other appropriate excipients may be similarly used.

In a separate embodiment, the enteric coating comprises: (a) cellulose acetate phthalate, (C-A-P) cellulose acetate trimellitate (C-A-T), Hydroxypropyl Methylcellulose Acetate Succinate (HPMCAS), Hydroxypropyl Methylcellulose phthalate (HPMCP), polyvinyl acetate phthalate (PVAP), Anionic phthalate polymers based on methacrylic acid and methacrylic acid esters; (b) compounds either alone or in any combination in organic solvent, (i.e isopropyl alcohol, methanol, ethanol or ethyl acetate) containing at least one plasticizer (i.e. triethyl citrate, polyethylene glycol 6000 or glycerol monostearate, as a coating solution; (c) the group of compounds in (a) either alone or in any combination in aqueous dispersion containing at least one plasticizer can be an alternative coating solution; and (d) the process to apply the coating solution or dispersion to said capsules or tablets is a conventional pharmaceutical method. The coating procedures are performed in a suitable coating machine.

This invention provides a process for manufacturing the capsule dosage form of above described drug which comprises steps of: (a) preparing the granulation by preferably dry mixing the active ingredient and alkaline substance(s) or by non-aqueous wet granulation method using only the pharmaceutically acceptable organic solvent, preferably methanol, ethanol or isopropyl alcohol as wetting solution and drying the granulation; (b) filling the capsule with the dried granulation; and (c) coating the capsules with an enteric coating solution or dispersion solution described above.

This invention provides a aqueous-free process for manufacturing the tablet dosage form that comprises steps of (a) preparing the granulation by preferably dry mixing the active ingredient and alkaline substance or pharmaceutical excipients; (b) directly compressing the granulation into a tablet by a conventional method; (c) filling the tablet into an empty hard gelatin capsule shell and; (d) coating the capsule with an enteric coating.

This invention provides an improved pharmaceutical dosage form for oral administration to human being or animal host containing an acid-unstable drug active ingredient which comprises: (a) a core tablet formed by dry mixing drug or its salt with alkaline substance and pharmaceutical excipient or excipients and directly compressing, which can be coated with a protective layer as a barrier to: (i) separate the acid-unstable active drug in the core from the outer enteric coating; and (ii) protect the entered coating from the permeation of alkaline solution formed by water in the core tablet; and (b) an enteric coating disposed on said protectively coated tablet to protect it from releasing the acid-unstable drug in the stomach and to deliver the active to the small intestine. In an emobodiment of the above process for manufacturing the improved pharmaceutical dosage form, the core granulation is prepared by dry mixing, direct tablet compressing, subcoating the tablet with organic solvent base protective coating; and coating the subcoated tablets with an enteric coating solution or dispersion.

This invention provides an improved pharmaceutical dosage form for oral administration to human being or animal host containing an acid-unstable drug active ingredient which comprises: (a) a core tablet formed by dry mixing drug or its salt with alkaline substance and pharmaceutical excipient or excipients and directly compressing, which can then be coated with a protective layer as a barrier to: (i)separate the acid-unstable active drug in the core from the outer enteric coating; and (ii) protect the enteric coating from the permeation of alkaline solution formed by water in the core tablet; (b) an enteric coating disposed on said protectively coated tablet to prevent it from releasing the acid-unstable drug in the stomach and to deliver the active to the small intestine; and (c) this tablet is then filled into an empty hard gelatine capsule shell to form a final dosage form. In an embodiment of the above process for manufacturing the improved pharmaceutical dosage form, the core granulation is prepared by dry mixing, direct tablet compressing, subcoating the tablet with organic solvent base protective coating, coating the subcoated tablets with an enteric coating solution or dispersion and filling the said enteric coated tablet into an empty hard gelatin capsule.

EXAMPLE 1

Core Granulations: Non-Aqueous Wet Granulation:
A. Ten grams of omeprazole were granulated with 10 ml. of ethyl alcohol with agitation. The moist granules were dried and screened to obtain a uniform granule size.
B. A suspension of Omeprazole being 10 grams in 50 ml. of ethyl alcohol was added into 100 grams of an alkaline inert compound being calcium carbonate granules (DELAVAU, Philadelphia, Pa.) with agitation to mix homogeneously the liquid and solids. The moist granules were dried and screened for uniform and adequate granule size.
C. Same as Example 1.B., except the alkaline substance is calcium carbonate 90A (Particle Dynamics, Inc., St. Louis, Mo.)
D. A mixture of 16 grams of Omeprazole and 10 grams of povidone USP was dispersed in 15 ml. of ethyl alcohol. The rest of the procedure is same as Example 1.B. above except that the dispersion was used to replace the suspension for 84 grams of alkaline substance.
E. Ten grams of sodium carboxymethylcellulose was dispersed in 10 ml. of ethyl alcohol. This liquid was then used to granulate a mixture of 2 grams of Omeprazole and 5 grams of calcium carbonate 90A (same as that used in Example 1.C.). The remaining portion of the procedure is the same as Example 1.B. above.

EXAMPLE 2

Core Granulation: Dry Mixing:
A. Ten grams of Omeprazole were mixed with an alkaline substance being tricalcium phosphate anhydrous USP/NF and then passed through a screen to obtain a homogenous granule size.
B. Same Example 2.A. above except the alkaline substance is pharmaceutical excipient microcrystalline cellulose USP/NF.
C. Same as Example 2.A. above except the alkaline substance is pharmaceutical excipient lactose, anhydrous USP.
D. Same as Example 2.A. above except the alkaline substance is pharmaceutical excipient maltodextrin.
E. Same as Example 2.A. above except the alkaline substance is Calcium Carbonate 90A (same as Example 1.C. above).
F. Same as Example 2.A. above except the alkaline substance is Calcium Carbonate granules (same as Example 1.B. above).
G. Same as Example 2.A. above except the alkaline substance is Sodium carboxymethylcellulose.

EXAMPLE 3

Encapsulation:
The individual core granulation was mixed with 2% to 5% talc used as a lubricant, and then quantitatively encapsulated in hard gelatin capsules by known pharmaceutical techniques.

EXAMPLE 4

Direct Tablet Compression:
A. The individual core granulation was mixed with Lactose and Talc or magnesium stearate, and compressed into tablets by known pharmaceutical techniques.

EXAMPLE 5

Capsule Enteric Coating:
The hard gelatine capsules obtained from Example 3. above were enteric coated in a conventional film coating machine with the following coating solutions by known pharmaceutical techniques.

| | |
|---|---|
| Eudragit L-100 ® (Methacrylic Acid Copolymer) | 600 Grams |
| Isopropyl Alcohol | 8,600 Grams |
| Triethyl Citrate | 60 Grams |
| FD&C or D&C aluminum laks | 300 Grams |
| Purified water | 400 Grams |

EXAMPLE 6

A. Tablet Protective Coating:

The tablets obtained from Example 4. were coated in a conventional film coating machine with the following coating solution by known pharmaceutical techniques.

| | | |
|---|---|---|
| Methocel E15 ® (Hydroxypropylmethylcellulose) | 500 | Grams |
| Polyethylene Glycol E400 | 110 | Grams |
| Ethyl Alcohol | 10,000 | Grams |

B. Enteric Coating for Tablets:

The coated tablets obtained from Example 6.A. were enteric coated in a conventional film coating machine with the coating solution being the same as that used in Example 5. by a known pharmaceutical technique.

EXAMPLE 7

Coated Tablet in a Capsule:

The coated tablets obtained from Example 6.B. were encapsulated in empty hard gelatin capsules to form a capsule product.

EXAMPLE 8

Several formulations were placed in ambient room temperature conditions for stability studies. The color changes of the core granulations were observed. Some of the formulations are assayed using USP High Pressure Liquid Chromatographic (HPLC) methods to determine the amount of drug remaining. The results are shown on Table 1. below.

TABLE 1

| Example Omeprazole Number | Stabliity Time Period (Months) | Color Change | % of Remaining |
|---|---|---|---|
| 1.A. | 26 | + | N/A |
| 1.B. | 26 | 0 to + | 99.8 |
| 1.C. | 26 | 0 to + | 65.1 |
| 1.D. | 26 | 0 to + | 96.3 |
| 1.E. | 11 | +++ | N/A |
| 2.A. | 13 | 0 | 89.6 |
| 2.B. | 13 | 0 | N/A |
| 2.C. | 11 | + | 91.0 |
| 2.D. | 11 | ++ | 88.2 |
| 2.E. +3 | 11 | 0 to + | 33.6 |
| 2.F. +3 | 11 | 0 to + | 97.8 |
| 2.G. | 11 | 0 | 96.2 |
| 2.C. +4 | 11 | 0 to + | N/A |
| 2.F. +3 +5 | 11 | 0 to + | 96.4 |
| 2.F +6 +7 | 11 | 0 to + | 95.5 |

0 = no change
+ = intensity of color change
N/A no assay was performed

What is claimed is:

1. A pharmaceutical dosage form for oral administration to human being or animal host which consists essentially of:
   (a) a core granulation formed by dry mixing, without using an aqueous granulation solution, an acid-unstable drug with an alkaline substance and a pharmaceutical excipient or excipients, wherein the core granulation is capable of being quantitatively filled into an empty hard gelatin capsule shell having an outer surface and an inner surface, wherein the hard gelatine capsule shell separates the core granulation from an enteric coating, and wherein the acid-unstable drug is omeprazole, sodium omeprazole, potassium omeprazole, lansoprazole, or a pharmaceutical salt of lansoprazole; and
   (b) the enteric coating being disposed on the outer surface of the hard gelatin capsule shell to prevent the release of the acid-unstable drug in the gastric environment and to deliver the acid-unstable drug in the intestinal environment, wherein the pharmaceutical dosage form has more than about 95% of the drug remaining after 11 months in ambient room temperature conditions.

2. A pharmaceutical dosage form for oral administration to human being or animal host which consists essentially of:
   (a) a core tablet formed by dry mixing, without using an aqueous solution, an acid-unstable drug with an alkaline substance and a pharmaceutical excipient or excipients and then by direct compression, wherein the core tablet is capable of being filled into an empty hard gelatin capsule shell having an outer surface and an inner surface, wherein the hard gelatin capsule shell separates the core tablet from an enteric coating, and wherein the acid-unstable drug is omeprazole, sodium omeprazole, potassium omeprazole, lansoprazole, or a pharmaceutical salt of lansoprazole; and
   (b) the enteric coating being disposed on the outer surface of the hard gelatin capsule shell to protect the acid-unstable drug in the gastric environment and to deliver the acid-unstable drug in the intestinal environment, wherein the pharmaceutical dosage form has more than about 95% of the drug remaining after 11 months in ambient room temperature conditions.

3. A pharmaceutical dosage form for oral administration to human being or animal host which consists essentially of:
   (a) a core tablet formed by dry mixing, without using an aqueous solution, an acid-unstable drug with an alkaline substance and a pharmaceutical excipient or excipients and then by direct compression, wherein the acid-unstable drug is omeprazole, sodium omeprazole, potassium omeprazole, or a pharmaceutical salt of lansoprazole, and wherein the core tablet is subcoated with a protective layer as a barrier to:
      (i) separate the acid-unstable active drug in the core tablet from an enteric coating; and
      (ii) protect the enteric coating from the permeation of alkaline solution formed in the core tablet; and
   (b) the enteric coating being disposed on the protectively subcoated tablet to protect the coated tablet from releasing the acid-unstable drug in the stomach and to deliver the acid-unstable drug to the small intestine, wherein the pharmaceutical dosage form has more than about 95% of the drug remaining after 11 months in ambient room temperature conditions.

4. The pharmaceutical dosage form according to claim 1, 2 or 3 wherein the alkaline substance is selected from one or any combination of the group consisting of alkaline metallic salt of carbonic acid, calcium carbonate, granulated calcium carbonate, dicalcium phosphate anhydrous, dibasic sodium phosphate anhydrous, tricalcium phosphate anhydrous, sodium carboxymethylcellulose, calcium carboxymethylcellulose, magnesium aluminum silicate, sodium lauryl sulfate and sodium bicarbonate.

5. The pharmaceutical dosage form according to claim 1, 2 or 3 wherein the pharmaceutical excipient is selected from one or any combination of the group consisting of dextrose, sorbitol, mannitol, starch, dextrin, maltodextrin, lactose, magnesium stearate, calcium stearate, talc, microcrystallinecellulose, hydroxypropylmethylcellulose and hydroxyethylcellulose.

6. The pharmaceutical dosage form according to claim 1, 2 or 3 wherein the enteric coating comprises:
(a) enteric polymer selected from the group consisting of cellulose acetate phthalate, cellulose acetate trimellitate, hydroxypropyl methylcellulose acetate succinate, hydroxypropyl methylcellulose phthalate, polyvinyl acetate phthalate, anionic polymers based on methacrylic acid and methacrylic acid esters;
(b) organic solvent selected from the group consisting of isopropyl alcohol, methanol, ethanol and ethyl acetate; to make polymer solution and aqueous system to make aqueous dispersion of polymer; and
(c) plasticizer selected from the group consisting of triethyl citrate, polyethylene glycol 6000 and glycerol monostearate.

7. The pharmaceutical dosage form according to claim 3 wherein the protective layer comprises:
(a) non-ionic protective polymer selected from the group consisting of hydroxypropyl methylcellulose, hydroxyethyl cellulose, and hydroxypropyl cellulose polyvinylpyrrolidone;
(b) organic solvent selected from the group consisting of isopropyl alcohol, methanol and ethanol; and
(c) plasticizer selected from the group consisting of triethyl citrate, propylene glycol and polyethylene glycol 6000.

8. An oral pharmaceutical preparation consisting essentially of:
(a) a core formulation comprising an acid-unstable drug and an alkaline substance, formed by dry mixing without using an aqueous granulating solution, wherein the acid-unstable drug is omeprazole, sodium omeprazole, potassium omeprazole, lansoprazole, or a pharmaceutical salt of lansoprazole;
(b) a hard gelatin capsule shell housing the core formulation, wherein the gelatin capsule shell has an outer surface and an inner surface; and
(c) an enteric coating disposed on the outer surface of the hard gelatin capsule, wherein the enteric coating is separated from the core formulation by the hard gelatin capsule shell without a protective coating.

9. The oral pharmaceutical preparation of claim 8, wherein the core formulation further comprises a pharmaceutical excipient.

10. The pharmaceutical dosage form according to claim 9 wherein the pharmaceutical excipient is selected from one or any combination of the group consisting of dextrose, sorbitol, mannitol, starch, dextrin, maltodextrin, lactose, magnesium stearate, calcium stearate, talc, microcrystallinecellulose, hydroxypropylmethylcellulose and hydroxyethylcellulose.

11. The oral pharmaceutical preparation of claim 8, wherein the core formulation is in the form of powder or granules.

12. The oral pharmaceutical preparation of claim 8, wherein the core formulation is in the form of a tablet.

13. The pharmaceutical dosage form according to claim 8 wherein the alkaline substance is selected from one or any combination of the group consisting of alkaline metallic salt of carbonic acid, calcium carbonate, granulated calcium carbonate, dicalcium phosphate anhydrous, dibasic sodium phosphate anhydrous, tricalcium phosphate anhydrous, sodium carboxymethylcellulose, calcium carboxymethylcellulose, magnesium aluminum silicate, sodium lauryl sulfate and sodium bicarbonate.

14. The pharmaceutical dosage form according to claim 8 wherein the enteric coating comprises:
(a) enteric polymer selected from the group consisting of cellulose acetate phthalate, cellulose acetate trimellitate, hydroxypropyl methylcellulose acetate succinate, hydroxypropyl methylcellulose phthalate, polyvinyl acetate phthalate, anionic polymers based on methacrylic acid and methacrylic acid esters;
(b) organic solvent selected from the group consisting of isopropyl alcohol, methanol, ethanol and ethyl acetate; to make polymer solution and aqueous system to make aqueous dispersion of polymer; and
(c) plasticizer selected from the group consisting of triethyl citrate, polyethylene glycol 6000 and glycerol monostearate.

\* \* \* \* \*